United States Patent [19]

DePasquale et al.

[11] Patent Number: 4,645,846
[45] Date of Patent: Feb. 24, 1987

[54] SILANE COMPOSITIONS

[75] Inventors: Ralph J. DePasquale; James M. Evans, both of Jacksonville; Paul W. Kremer, Gainesville, all of Fla.

[73] Assignee: SCM Corporation, New York, N.Y.

[21] Appl. No.: 722,325

[22] Filed: Apr. 12, 1985

[51] Int. Cl.$^4$ .......................... C07F 7/10; C07F 7/18
[52] U.S. Cl. ................................ 556/419; 556/421; 427/387; 427/388.1; 427/409; 106/14.15; 106/14.05; 252/389.31
[58] Field of Search ............... 556/419, 421; 427/387, 427/388.1, 409; 106/14.15, 14.05; 252/389 R

[56] References Cited

U.S. PATENT DOCUMENTS

| | | | |
|---|---|---|---|
| 2,907,782 | 10/1959 | Pike | 556/421 |
| 2,919,173 | 12/1959 | Roff | 556/419 X |
| 3,629,309 | 12/1971 | Bailey et al. | 556/419 |
| 3,759,751 | 9/1973 | Smith | 148/6.2 |
| 3,890,269 | 6/1975 | Martin | 260/46.5 E |
| 4,209,455 | 6/1980 | Pepe | 556/419 |
| 4,217,294 | 8/1980 | Petty | 556/419 |
| 4,310,575 | 1/1982 | Khayat | 427/409 |
| 4,434,161 | 2/1984 | Barcza | 556/419 X |

FOREIGN PATENT DOCUMENTS 1409483 10/1975 United Kingdom ........ 556/419 UX

Primary Examiner—Paul F. Shaver
Attorney, Agent, or Firm—R. A. Sturges

[57] ABSTRACT

There is provided a corrosion inhibiting alkoxy silane characterized by an alkyleneamino group attached to silicon through a Si—C linkage, a carbonyl or thiocarbonyl group attached to an amine group and a terminal group which may be saturated or unsaturated aliphatic or cycloaliphatic group containing 6 to 20 carbon atoms, a saturated or unsaturated aminoaliphatic or amino cycloaliphatic group containing 6-20 carbon atoms; $NHNH_2$; $NH(CH_2)_nN(R)_2$; or a

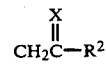

group where $R^2$ is a saturated or unsaturated alkyl or haloalkyl group containing 3 to 20 carbon atoms. The invention also provides a method of inhibiting corrosion of metal surfaces by applying a coating containing or consisting of a novel silane as above described.

24 Claims, No Drawings

SILANE COMPOSITIONS

This invention relates to novel silanes characterized by an alkylene group attached to silicon at one end and functional groups at the other end including amine or amide and carbonyl or thiocarbonyl. These materials have special utility as corrosion inhibitors for metal, particularly iron and steel.

BACKGROUND OF THE INVENTION AND PRIOR ART

The degradative attack of a metal by its environment through chemical or electrochemical means is a description of the corrosive process. The literature deals extensively with agents that retard corrosion of metal surfaces. Using iron as a representative metal, corrosion has been viewed to occur at sites consisting of electromotive cells. The anode region converts iron to iron (II) with electron liberation. To maintain electrical neutrality, the cathode region finds protons (hydronium ions) capturing electrons evolving hydrogen under acid conditions or oxygen reduced to hydroxide in the presence of water under alkaline or neutral conditions. The ferrous hydroxide produced from the coupled electrochemical reaction is subsequently oxidized to ferric oxide, rust, which due to its larger expansion by comparison to iron metal ruptures and fails to form a protective layer on the iron surface.

Agents that interfere with any of the above critical steps in the corrosion cycle act as inhibitors. The present invention will describe novel compounds that contain two structural features acting in concert to control corrosion. The first is an alkoxy silane that can form a passivating multidimensional cohesive film barrier capable of adhesive covalent bonding to the surface of many metals in the presence of moisture. The second is a carbon bound substitutent on the silicon center of the alkoxy silane, immobilized in molecular proximity to the metal surface by the above described bonding and designed to act as either a resistive/hydrophobic, pH control, ion immobilizing or free radical inhibiting center. The examples below demonstrate the synthesis of these materials and their corrosive reducing properties when applied to iron surfaces.

The use of silanes to inhibit corrosion of iron or steel is not broadly new. Representative examples of prior disclosures include U.S. Pat. No. 3,890,269 to Martin teaches the preparation of aminofunctional organopolysiloxanes which are said to be useful as sizing agents and as corrosion inhibitors. U.S. Pat. No. 3,759,751 discloses a wash primer comprising an epoxy resin, an inorganic chromate, and an aminosilane for use on aircraft surfaces. British Pat. No. 1,409,483 discloses methylaminoethyltriethoxysilane as a corrosion inhibitor for nonferrous metals and alloys. U.S. Pat. No. 4,310,575 to Khayat discloses trimethylsilylacetamide as a corrosion inhibitor for steel. The present invention provides novel silane compounds which have utility as corrosion inhibitors for metal surfaces.

BRIEF STATEMENT OF THE INVENTION

Briefly stated, the present invention is in novel silanes having the general formula:

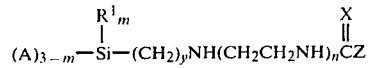

wherein A is a hydrolyzable group, $R^1$ is selected from alkyl groups containing from 1 to 3 carbon atoms, X is a chalcogen, n is 0-3, y is 2-4 and Z is selected from saturated or unsaturated aliphatic or cycloaliphatic groups containing from 6 to 20 carbon atoms; NH-saturated or unsaturated aliphatic or cycloaliphatic groups containing from 6 to 20 carbon atoms: $NHNH_2$; $NH(CH_2)_nN(R)_2$; and

where $R^2$ is saturated or alkyl or haloalkyl group containing from 1 to 20 carbon atoms. The preferred hydrolyzable groups include alkoxy groups containing 1 to 3 carbons, oximino and amino groups.

This invention is also in a method of inhibiting corrosion of a metal substrate by applying to the surface a thin coating (<0.001") of a silane having the above general formula.

The term "aliphatic" shall be deemed to include cycloaliphatic.

DETAILED DESCRIPTION AND SPECIFIC EXAMPLES

The novel compounds of the present invention are broadly lower alkyl, lower alkoxy, or mixed lower alkyl and lower alkoxy silanes characterized by an alkyleneamino group attached to the silicon atom by a Si—C linkage, a carbonyl or thiocarbonyl group attached to an amine group, and a terminal group which may be a saturated or unsaturated aliphatic or cycloaliphatic group containing 6-20 carbon atoms; a saturated or unsaturated amino aliphatic or cycloaliphatic group containing 6-20 carbon atoms; $NHNH_2$; $NH(CH_2)_nN(R)_2$; or a

group where $R^2$ is a saturated or unsaturated alkyl or haloalkyl group containing 3 to 20 carbon atoms.

Typical examples of silane compounds within the above class of novel compounds are as follows: In these examples, Me=methyl, Et=ethyl, Pr=propyl or isopropyl, $\phi$=phenyl, and $C_6H_{11}$=cyclohexyl.

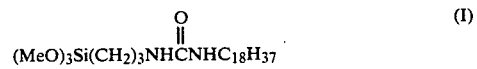

(I)

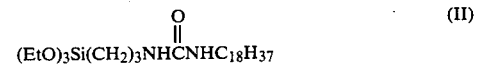

(II)

(III)

(IV)

-continued

 (V)

 (VI)

 (VII)

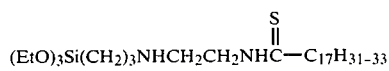 (VIII)

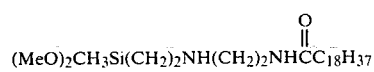 (IX)

 (X)

 (XI)

 (XII)

 (XIII)

 (XIV)

 (XV)

 (XVI)

 (XVII)

 (XVIII)

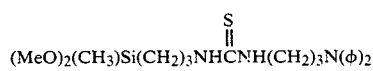 (XIX)

 (XX)

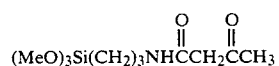 (XXI)

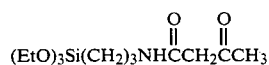 (XXII)

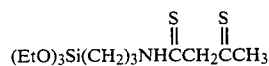 (XXIII)

 (XXIV)

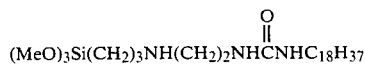 (XXV)

-continued

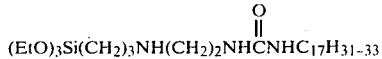 (XXIV)

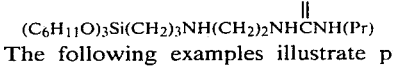 (XXVII)

p The following examples illustrate procedures by which members of the foregoing typical examples may be prepared. The roman numerals given in these examples correspond to those given above.

EXAMPLE 1

Preparation of N-Octadecyl-N'-(3-Triethoxysilyl)Propyl Urea (II)

To 44 g (0.20 mole) of 3-aminopropyltriethoxysilane was added 59 g (0.20 mole) of octadecylisocyanate with stirring; the resulting exotherm brought the temperature of the solution to 110° C. Cooling to ambient temperature afforded 93 g (100% yield) of a waxy white solid, m.p. 43°–45° C. IR (neat film) 3300, 2900, 1600, 1470, 1380, 1280, 1100, 950, 790 cm$^{-1}$. NMR (CDCl$_3$) 0.4–1.0 (m; 5H), 1.0–1.8 (m; 43H), 2.9–3.3 (m; 4H), 3.55 (q; 6H), 6.3 (br; 2H) ppm. On corrosion tests on cold rolled steel (CRS) this material gave superior results and is the best mode for carrying out our invention.

EXAMPLE 2

Preparation of N-Octadecyl-N'-(3-Trimethoxysilyl)Propyl Urea (I)

The trimethoxy analogue of Example I is prepared by the procedure of Example I. 3-Aminopropyltrimethoxysilane is substituted on a mole for mole basis for the 3-aminopropyltriethoxysilane of Example I.

EXAMPLE 3

Preparation of N-Heptadecyl or Heptadecylene-N'-(3-Dimethoxymethylsilyl)-Propyl Urea (IV)

To 32.6 g (0.20 mole) of 3-aminopropyldimethoxymethylsilane are added (0.20 mole) tall oil fatty acid derived isocyanate with stirring; the exotherm results in a temperature of about 110° for the resulting solution. On cooling to room temperature a waxy solid is obtained.

EXAMPLE 4

Preparation of Tall Oil Fatty Acid Amide of 3-(2-Aminoethylamino)Propyl-Trimethoxysilane (VII)

To a solution of 3-(2-aminoethylamino)propyltrimethoxysilane (232 g, 1.04 mole) was added 310 g (1.04 mole) of tall oil methyl-C$_{18}$-esters. The solution was slowly heated to 50° C. and 4 ml of 25% sodium methoxide in methanol was added. Heating was continued to 170° C. while continuously removing methanol. Cooling to ambient temperature afforded 500 g (101%) of dark yellow oil. IR (neat film) 3300, 2930, 2860, 1650, 1610, 1550, 1460, 1190, 1080, 825 cm$^{-1}$. NMR (CDCl$_3$) 0.4–1.0 (m; 5H), 1.0–1.8 (m; 24H), 1.8–2.4 (m; 8H), 2.4–2.9 (m; 4H), 3.0–3.3 (m; 2H), 3.55 (br s; 9H), 5.2–5.5 (m; ca. 2H), 6.9 (br s; 1H) ppm.

EXAMPLE 5

Preparation of Tall Oil Thio-Fatty Acid Amide of 3-(2-Aminoethylamino)-Propyl Triethoxysilane (VIII)

Following the procedure of Example 4 and substituting for the 3-(2-aminoethylamino)propyltrimethoxysilane an equivalent amount of 3-(2-aminoethylamino)-propyltriethoxysilane, and for the tall oil esters, an equivalent amount of the corresponding thionic esters of tall oil fatty acids, there is obtained the titled compound.

EXAMPLE 6

Preparation of Tall Oil Fatty Acid Amide of 3-Aminopropyltriethoxysilane (X)

To 230 g (1.04 mole) of 3-aminopropyltriethoxysilane was added 310 g (1.04 mole) of tall oil methyl-$C_{18}$-esters. The solution was slowly heated to 50° C. and 4 ml of 25% sodium methoxide in methanol was added. Heating was continued to 170° C. while continuously removing alcohols. Cooling to ambient temperature afforded a viscous oil; flash distillation at 220°/0.1 torr gave 380 g (75% yield) of yellow oil. IR (neat film) 3300, 2930, 2860, 1645, 1550, 1105, 1080, 960, 790 cm$^{-1}$. NMR (CDCl$_3$) 0.4–1.0 (m; 5H), 1.0–1.8 (m; 35H), 1.8–2.5 (m; 6H), 3.25 (br q; 2H), 3.82 (q; 6H), 5.2–5.6 (m; ca. 2H), 6.1 (br t; 1H) ppm.

EXAMPLE 7

Preparation of 4-(3-Triethoxysilylpropyl)Semicarbazide (XII)

A mixture of 44.2 g (0.20 mole) 3-aminopropyltriethoxysilane and 18.0 g (0.20 mole) methyl hydrazinocarboxylate under nitrogen was gradually heated to 150° C. with a slow distillation of the evolved methanol/ethanol from the reaction. After 2 hours at 150° C., 9.1 g. of distillate had been collected, and the reaction mass was cooled to ambient. The pale yellow oil was decanted from the small amount of white solid; yield 51 g (91%). IR (neat) 3320, 1640 (br), 1540 (br), 1070 (br), 940, 790 cm$^{-1}$. NMR (CDCl$_3$) 0.4–1.0 (m; 2H), 1.2 (t; 9H), 1.3–2.0 (m; 2H), 2.9–3.5 (m; 2H), 3.5–4.1 (m; 8H), 6.3 (br; 2H) ppm.

EXAMPLE 8

Preparation of N-(3-Dimethylaminopropyl)-N'-(3-Triethoxysilyl-propyl)Urea (XVI)

To a stirred solution of 3-isocyanatopropyltriethoxysilane (74 g; 0.31 mole) was slowly added 30 g (0.30 mole) of N,N-dimethyl-1,3-propanediamine. There was a significant exotherm. The product was purified by strip distillation at 205° C. (0.1 torr). NMR (CDCl$_3$) 0.40–0.9 (m; 2H), 1.22 (t; 9H), 1.4–1.9 (m; 4H), 2.21 (s; 6H), 2.33 (t; 2H), 2.9–3.4 (m; 4H), 3.81 (q; 6H), 5.8 (b, 2H) ppm. IR (neat film) 3340, 2980, 2940, 1635, 1575, 1105, 1080, 960, 780 cm$^{-1}$.

EXAMPLE 9

Preparation of N-(3-Dimethylaminopropyl)-N'-(3-Trimethoxysilyl-propyl)Urea (XV)

The titled product is produced as in Example 8 substituting for the 3-isocyanatopropyltriethoxy silane an equivalent amount of the corresponding 3-isocyanatopropyltrimethoxysilane.

EXAMPLE 10

Preparation of N-(3-Triethoxysilyl)-Propyl-Beta-Oxobutyramide (XXII)

A solution of 22.1 g (0.10 mole) of 3-aminopropyltriethoxysilane in 100 ml of CHCl$_3$ was cooled to 0° C. (internal temperature) in an ice-acetone bath. A 50% solution of diketene in acetone (16.8 g; 0.10 mole) was added dropwise over a 20 min. period, maintaining the internal temperature at 0°–5° C. The reaction was stirred at 20° C. for 17 hr. before it was stripped of solvent at 45° C./30 torr. A mobile, pale yellow oil weighing 32.9 g was obtained. IR (neat film) 3300, 3080 (w), 2980, 1720, 1650, 1545, 1105, 1080, 960, 780 cm$^{-1}$. NMR (CDCl$_3$) 0.4–0.8 (m; 2H), 1.22 (t; 9H), 1.4–1.9 (m; 2H), 2.25 (s; 3H), 3.25 (br q; 2H), 3.38 (s; 2H), 3.80 (q; 6H), 7.30 (br t; 1H) ppm.

EXAMPLE 11

Preparation of N-Octadecyl-N'-2-(3-Trimethoxysilyl-propylamino)Ethyl Urea (XXV)

To 22.2 g (0.10 mole) of 3-(2-aminoethylamino)-propyltrimethoxysilane under nitrogen was added 29.5 g (0.10 mole) of octadecylisocyanate over a 45 min. period. The reaction temperature rose to ca. 70° C. Upon cooling to ambient temperature, the product solidified to a white wax. IR (neat film) 3300, 2900, 1620, 1570, 1470, 1090 cm$^{-1}$. NMR (CDCl$_3$) 0.4–1.0 (m; 5H), 1.1–2.0 (m; 34H), 2.4–2.8 (m; 2H), 2.9–3.4 (m; 7H), 3.55 (s; 9H), 5.5 (br s; 2H) ppm.

Specimen Preparation and Testing Procedure

A 0.5, 1, 2 or 5% (by weight) of the silane corrosion inhibitor (Roman Numeral) solution was prepared in 10% aqueous ethanol. A 2"×4" metal specimen of non-phosphated cold rolled steel (CRS), or phosphated cold rolled steel (Phos-CRS), was dipped into the inhibitor solution, air dried, then oven dried at 90° C. for 30 minutes, and cooled to ambient temperature. The treated specimen was attached to a Princeton 350A corrosion meter cell as the working electrode. The cell uses a standard calomel electrode as reference and two high density graphite rods as counter electrodes. Tap water and in some cases, 5% aqueous NaCl served as test solutions. The above potentiodynamic polarization technique provides data based on current-potential plots from which can be derived corrosion potentials, corrosion currents and corrosion rates of specimens treated with inhibitors relative to controls. Details for carrying these measurements will be found in the Journal of Coatings Technology, Volume 56, No. 714, July 1984, pages 31–41, in an article by R. G. Groseclose et al.

Electrochemical Technique of Corrosion Tests

According to the procedure described in the article by Groseclose et al, supra, a PAR Model 350A was used to evaluate the corrosion rate of specimens using a technique called "Polarization Resistance" (or "Linear Polarization"). A measurement is performed by scanning through a potential range which is very close to the corrosion potential, $E_{corr}$ (the potential at which the rate of oxidation is exactly equal to the rate of reduction). In these experiments, the range was ±25 mV about $E_{corr}$. The resulting current is plotted versus potential. The slope of the curve at $E_{corr}$ allows a determination of the corrosion current density, $I_{corr}$. The value for $I_{corr}$ was used to calculate the absolute corrosion rate, expressed in milli-inches (0.001 in.) per year (MPY).

While all examples demonstrate an ability to inhibit corrosion of steel, several samples provided significant corrosion inhibition: Example 4 (VII); Example 6 (X); Example 7 (XII) and Example 10 (XXII). Two of these (Example 4 (VII) and Example 6 (X)) have fatty acid residues in their structures, so stearic acid and hexadecylamine were run as controls, but they showed no corrosion inhibition. In fact, hexadecylamine gave the highest rate of corrosion of all samples tested.

The ability of the silane compound to chelate with iron may be adventitious. An example of this is Example 10 (XXII). Synthesis of chelating silanes with fatty acid residues is a reasonable objective for cost reasons.

SUMMARY OF CORROSION TEST RESULTS[a]

| Treatment Solution | CRS Tap Water | CRS 5% NaCl | Phos-CRS 5% NaCl |
| --- | --- | --- | --- |
| Control - 1% aq. EtOH[b] | 5.1 mpy | 16.5 mpy | 5.8 mpy |
| Control - 10% aq. EtOH | 4.5 | 12.0 | 7.2 |
| "Chrome Rinse"[c] | | | 18.6 |
| 0.5% (II)[b] | 0.53 | | |
| 2.0% (II)[b] | 0.008 | 10.2 | 0.022 |
| 1.0% (VII) | 0.36 | | |
| 5.0% (VII) | 0.43 | 5.6 | 2.1 |
| 1.0% (X) | 0.32 | 3.0 | |
| 5.0% (X) | 0.16 | 2.9 | 1.6 |
| 1.0% (XII) | 0.44 | | |
| 5.0% (XII) | 0.61 | 12.5 | 4.2 |
| 5.0% (XVI) | 7.1 | | |
| 1.0% (XXII) | 0.52 | | |
| 5.0% (XXII) | 0.33 | 3.7 | 4.3 |
| 0.5% (XXV)[b] | 0.085 | 14.3 | |
| 2.0% (XXV)[b] | 0.018 | 1.2 | |

[a]Results are in mils-per-year (mpy).
[b]The sample was treated in 1% aq. EtOH at the boil; all others were from 10% aq. EtOH at room temperature.
[c]A commercially prepared sample of cold-rolled steel (CRS) that had been phosphated and chromated.

There has thus been provided a novel class of silanes containing amino and/or amido groups and one or more carbonyl or thiocarbonyl groups which are particularly effective anticorrosion agents when applied as a coating to a metal substrate, particularly steel. These inhibitors may be used as primers on clean metal surfaces. Adhesion of top or finish coats will also be improved with these materials as additives.

What is claimed is:
1. A silane having the general formula:

$$(A)_{3-m}-\underset{\underset{R^1_m}{|}}{Si}-(CH_2)_y NH(CH_2CH_2NH)_n \overset{\overset{X}{\|}}{C}Z$$

wherein A is a hydrolyzable group, $R^1$ is selected from alkyl groups containing 1 to 3 carbon atoms, X is a chalcogen, m is 0 to 3, n is 0 to 3, y is 2 to 4, and Z is selected from saturated or unsaturated aliphatic or cycloaliphatic groups containing from 6 to 20 carbon atoms; NH-saturated aliphatic or cycloaliphatic groups containing 6 to 20 carbon atoms; NH-unsaturated aliphatic or cycloaliphatic groups containing 6–20 carbon atoms, $-NH-NH_2$, $NH-(CH_2)_nN(R)_2$, and $$-CH_2-\overset{\overset{X}{\|}}{C}R^2$$

where $R^2$ is a saturated or unsaturated alkyl or haloalkyl group containing 1 to 20 carbon atoms.
2. A silane as defined in claim 1 wherein m is 0.
3. A silane as defined in claim 1 wherein m is 3.
4. A silane as defined in claim 1 wherein y is 3.
5. A silane as defined in claim 1 wherein n is 0.
6. A silane as defined in claim 1 wherein X is oxygen.
7. A silane as defined in claim 1 wherein X is sulfur.
8. A silane as defined in claim 1 wherein m is 0, y is 3 and n is 0.
9. A silane as defined in claim 1 wherein m is 1, y is 3 and n is 0.
10. A silane as defined in claim 1 wherein m is 0, y is 3, n is 0 and X is oxygen.
11. A silane as defined in claim 10 which is N-octadecyl-N'-(3-trimethoxysilyl)propyl urea.
12. A silane as defined in claim 10 which is N-octadecyl-N'-(3-triethoxysilyl)propyl urea.
13. A silane as defined in claim 9 which is N-heptadecyl-N'-(3-dimethoxymethylsilyl)propyl urea.
14. A silane as defined in claim 9 which is N-heptadecylene-N'-(3-dimethoxymethylsilyl)propyl urea.
15. A silane as defined in claim 1 which is the tall oil fatty acid amide of 3-(2-aminoethylamino)propyl trimethoxysilane.
16. A silane as defined in claim 1 which is the tall oil thio fatty acid amide of 3-(2-aminoethylamino)propyl-triethoxysilane.
17. A silane as defined in claim 10 which is the tall oil fatty acid amide of 3-aminopropyltriethoxy silane.
18. A silane as defined in claim 1 which is 4-(3-triethoxysilylpropyl)semicarbazide.
19. A silane as defined in claim 1 which is N-(3-dimethylaminopropyl)-N'-(3-triethoxysilylpropyl)urea.
20. A silane as defined in claim 1 which is N-(3-dimethylaminopropyl)-N'-(3-trimethoxysilylpropyl)urea.
21. A silane as defined in claim 1 which is N-(3-triethoxysilylpropyl)-beta-oxobutyramide.
22. A silane as defined in claim 1 which is N-octadecyl-N'-2-(3-trimethoxysilylpropylamino)-ethyl urea.
23. The method of improving the resistance of iron or steel to corrosion which comprises applying to the surface thereof a silane having the general formula:

$$(A)_{3-m}-\underset{\underset{R^1_m}{|}}{Si}-(CH_2)_y NH(CH_2CH_2NH)_n \overset{\overset{X}{\|}}{C}Z$$

wherein A is a hydrolyzable group, $R^1$ is selected from alkyl groups containing 1 to 3 carbon atoms, X is a chalcogen, m is 0 to 3, n is 0 to 3, y is 2 to 4, and Z is selected from saturated or unsaturated aliphatic or cycloaliphatic groups containing from 6 to 20 carbon atoms; NH-saturated aliphatic or cycloaliphatic groups containing 6 to 20 carbon atoms; NH-unsaturated aliphatic or cycloaliphatic groups containing 6–20 carbon atoms, $-NH-NH_2$, $NH-(CH_2)_nN(R)_2$, and $$-CH_2-\overset{\overset{X}{\|}}{C}R^2$$

where $R^2$ is a saturated or unsaturated alkyl or haloalkyl group containing 1 to 20 carbon atoms.
24. The method of claim 23 wherein the silane is N-octadecyl-N'-(3-triethoxysilyl)propyl urea.

* * * * *